United States Patent [19]

Hayashi et al.

[11] Patent Number: 5,081,016

[45] Date of Patent: Jan. 14, 1992

[54] METHOD FOR MEASURING THE AMOUNT OF POLYAMINES IN A BIOLOGICAL SAMPLE

[75] Inventors: Yuzo Hayashi, Takarazuka; Haruo Watanabe, Kyoto, both of Japan

[73] Assignee: Toyo Boseki Kabushiki Kaisha, Osaka, Japan

[21] Appl. No.: 291,141

[22] Filed: Dec. 28, 1988

[30] Foreign Application Priority Data

Dec. 28, 1987 [JP] Japan .................. 62-335805

[51] Int. Cl.$^5$ .................. C12Q 1/32; C12Q 1/26
[52] U.S. Cl. .................. 435/25; 435/26; 435/810; 436/64; 436/175; 436/813; 436/815
[58] Field of Search .................. 435/25, 26, 810; 436/64, 175, 813, 815

[56] References Cited

FOREIGN PATENT DOCUMENTS 0184919 11/1985 European Pat. Off.
2204951 3/1988 United Kingdom.

OTHER PUBLICATIONS

Kusche et al., *Agents Actions*, Oct. 1973, 3(3), pp. 148–156, "Comparison of the $^{14}$C-Putrescine Assay with the NADH Test for the Determination of Diamine Oxidase".
Chemical Abstracts, vol. 110, No. 19, May 8, 1989, p. 44, Abstract No. 169814u, Columbus, Ohio, U.S.; H. Watanabe et al.: "Reducing substance removal from biological samples in optical analysis".
Methods of Enzymic Analysis, vol. 8, 1985, 3rd edition, pp. 566–572, Verlag-Chemie, DE.; S. Kubota et al.: "Polyamines".
Production of Extracellular Polyamine Oxidase by Penicillium sp. No. PO-1, Yoshinori Kobayashi and Koki Horikoshi, (1981).
The Journal of Biological Chemistry, vol. 234, No. 8 (Aug. 1959), pp. 2145–2150.
Biochimica Biophysica Acta, 705 (1982), pp. 133–138.
Biochimica Biophysica Acta, 743 (1983), pp. 431–436.
Agric. Biol. Chem., 50(8) (1986), pp. 2009–2016.
Nippon Nogeikagaku Kaishi, vol. 62, No. 3 (Mar. 15, 1988), pp. 131, 417.
Japanese Journal of Clinical Laboratory Automation, vol. 13, No. 4 (Aug. 1, 1989), pp. 410–412.

*Primary Examiner*—Robert A. Wax
*Assistant Examiner*—Laurie Scheiner
*Attorney, Agent, or Firm*—Wegner, Cantor, Mueller & Player

[57] ABSTRACT

A method for measuring the amount of polyamines in a biological sample is provided. The method comprises utilizing diamine oxidase and/or polyamine oxidase, aminoalkylaldehyde dehydrogenase and NAD$^+$ or NADPH$^+$, wherein the improvement comprises carrying out the method in the presence of an acidic aromatic compound.

6 Claims, 1 Drawing Sheet

METHOD FOR MEASURING THE AMOUNT OF POLYAMINES IN A BIOLOGICAL SAMPLE

BACKGROUND OF THE INVENTION

1. Field of the invention:

This invention relates to a method for measuring the amount of polyamines in a biological sample, and in particular, to a method for measuring the amount of polyamines in an urine sample, in which the polyamines can be measured accurately without being affected by interfering substances that may be present in the biological sample.

2. Description of the prior art:

The polyamines (including diamines) that are found in fluids from the body such as urine are known to be closely correlated to the onset of cancer and to the state of its progress. Eleven polyamines have been identified, including cadaverine, putrescine, spermidine, and spermine. Also, acylated forms of the said polyamines, i.e., acylpolyamines, have also been found. The measurement of total polyamines (below, the word "polyamines" is meant to include acylpolyamines) in fluids from the body and also the measurement of their individual levels have much clinical significance, because the values have been suggested to give information useful for the diagnosis of cancer. For that reason, a method is needed in which the amounts of polyamines can be measured with a high degree of accuracy.

In the conventional methods for measuring the amount of polyamines, polyamines in biological samples are isolated by the use of liquid chromatography or electrophoresis, and then measurement of the polyamines is done by a fluorescence method or by a colorimetric method with ninhydrin. However, these methods require the troublesome steps of pretreatment of the biological samples, and much time is needed for the measurement. For that reason, these methods cannot be used for carrying out the measurement of a large number of biological samples at once. In addition, these methods require special techniques, equipment, and facilities. Therefore, these methods cannot be used as, for example, routine procedures in clinical laboratories.

Japanese Laid-Open Patent Publication 56-36918 discloses a relatively simple method for measuring the amount of polyamines. In the method, polyamines are reacted with amine oxidase to produce hydrogen peroxide, and the hydrogen peroxide is reacted with 4-aminoantipyrin, phenol and peroxidase resulting in a pigment. The pigment is measured by colorimetric analysis. In this method, there is no need to isolate the polyamines from the biological samples in pure form by the use of liquid chromatography or electrophoresis. However, in this method, error arises because of the reducing substances present in the biological sample, so it is necessary to remove the reducing substances from the biological samples beforehand. For example, it is necessary to remove such reducing substances from the biological sample by passage of the biological sample through a column filled with a cation-exchange resin. Because of this pretreatment step, the polyamines in the biological sample cannot be measured in a single step by the use of an automated analyzer.

SUMMARY OF THE INVENTION

The method for measuring the amount of polyamines in a biological sample of this invention, which overcomes the above-discussed and numerous other disadvantages and deficiencies of the prior art, comprises utilizing diamine oxidase and/or polyamine oxidase, aminoalkylaldehyde dehydrogenase and $NAD^+$ or $NADPH^+$, wherein the improvement comprises carrying out the method in the presence of an acidic aromatic compound.

In a preferred embodiment, the method comprises the steps of adding a first reagent to the biological sample, said first reagent containing an acidic aromatic compound, and diamine oxidase and/or polyamine oxidase, so that the polyamines are converted into aminoalkylaldehydes; adding a second reagent to the reaction mixture, said second reagent containing aminoalkyldehydrogenase, and $NAD^+$ or $NADP^+$, so that the $NAD^+$ or $NADP^+$ is reduced to NADH or NADPH, respectively; and measuring either the amount of NADH or NADPH or the amount of products derived from the NADH or NADPH.

In a preferred embodiment, the first and second reagents are added to the biological sample simultaneously.

In a preferred embodiment, the method comprises the steps of, adding a first reagent to the biological sample, said first reagent containing an acidic aromatic compound, acylpolyamine amidohydrogenase, if necessary, aminoalkylaldehyde dehydrogenase and $NAD^+$ or $NADP^+$, so that acylpolyamines are converted to free polyamines and pre-existing aminoalkylaldehydes are oxidized with the formation of NADH or NADPH, respectively, as a blank reaction; adding a second reagent, said reagent containing diamine oxide and/or polyamine oxidase, so that the polyamines are converted into aminoalkylaldehyde and $NAD^+$ or $NADP^+$ is reduced to NADH or NADPH, respectively; and measuring either the amount of NADH or NADPH, or the amount of products derived from NADH or NADPH.

The present invention also comprises a reagent for measuring the amount of polyamines in a biological sample, that comprises diamine oxidase and/or polyamine oxidase, aminoalkylaldehyde dehydrogenase and $NAD^+$ or $NADP^+$, wherein an acidic aromatic compound is additionally present.

Thus, the invention described herein makes possible the objectives of: (1) providing a method for the accurate and simple measurement of polyamines in a biological sample, and of the polyamines in urine samples in particular; (2) providing a method for the accurate, rapid, and simple measurement of polyamines in urine samples without the need for a troublesome procedure for the separation of the polyamines from other substances that are also present in the biological samples, or without the need for special techniques, facilities, or apparatus; (3) providing a method for the measurement of polyamines that can be used widely in routine clinical tests because of its applicability to an automated analyzer; and (4) providing a method for the measurement of polyamines that can make a great contribution to various aspects of diagnosis and treatment in the field of clinical tests related to the onset of cancer.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
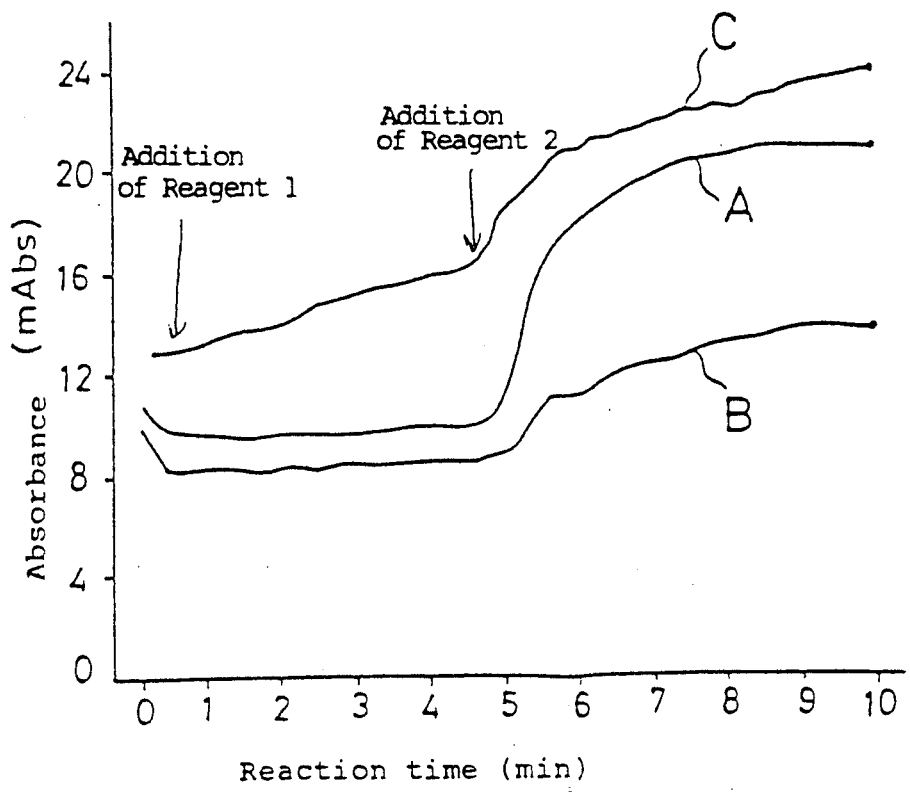
FIG. 1 is a graph that shows the relationships between reaction time and optical density at 570 nm of the reaction mixture when an urine sample is assayed for measuring polyamines with the method of this invention or a conventional method using an automated analyzer.

There are no particular restrictions as to the varieties of biological samples that can be assayed for polyamines by the method of this invention. Biological samples that can be employed include urine, blood, tissue, and the like. The method of this invention is especially suitable for the measurement of polyamines in urine samples.

Diamine oxidases (DAO) that are used in this invention are enzymes that can react with putrescine, cadaverine, spermidine, etc. An enzyme that is active toward putrescine as substrate that is called putrescine oxidase is particularly suitable. These DAOs can be of any origin; for example, DAO that is of vegetable origin, obtained from sprouted soy beans, from barley or wheat, etc.; DAO of animal origin obtained from pig kidneys or the like; or DAO of microbial origin obtained from Micrococcus species, Nocardia species, Aspergillus species, or the like can all be used. Polyamine oxidases (PAO) that are used in this invention are enzymes that can react with spermine and spermidine. These PAOs can be of any origin; for example, PAO that is of animal origin obtained from bovine plasma and the like, PAO of vegetable origin obtained from barley, etc.; and PAO of microbial origin obtained from Penicillium species, Aspergillus species, Streptomyces species, and the like can all be used (Biochemica et Biophysica Acta 743 (1983) 431-436; Biochemica et Biophysica Acta 705 (1982) 133-138; Agricultural and Biological Chemistry 45 (1981) 3943-3945).

The kind of aminoalkylaldehyde dehydrogenase is not restricted in any way, but aminobutylaldehyde dehydrogenase (abbreviated as ABAL-DH; EC 1.2.1.19) is particularly suitable. For example, ABAL-DH of microbial origin such as from Pseudomonas spp., etc. (J. Biol. Chem. 234 (1959) 2145-2150; Agri. Biol. Chem. 50 (1986) 2009-2016) can be used.

Acidic aromatic compounds that are used in this invention can be, for example, benzoic acid, naphthalenesulfonic acid, benzenesulfonate, benzenesulfate, or halogen derivatives or hydroxy derivatives of these compounds, etc. By the addition of these acidic aromatic compounds to the reaction system for the measurement of polyamines, reducing substances (for example, those that are present in urine) are inhibited from affecting the measurement system.

The measurement of polyamines in biological samples such as urine or the like by this invention can be carried out, for example, as follows. When the acylpolyamines contained in a biological sample are also to be measured, first, a solution that contains the biological sample is treated with acylpolyamineamidohydrolase (APAH) to convert the acylpolyamines into free polyamines by deacylation. There is no particular restriction as to the origin of the APAH. Next, this sample solution is treated with a reagent that contains DAO and/or PAO so as to convert the polyamines into aminoalkylaldehydes. To the reaction mixture, a reagent that contains aminoalkylaldehyde dehydrogenase, NAD+ or NADP+ (hereinafter referred to as NAD(P)+), and acidic aromatic compounds are added so as to convert the aminoalkylaldehydes in the sample solution into aminoalkylcarboxylic acids. At the same time, the NAD+ or NADP+ is changed to NADH or NADPH (hereinafter referred to as NAD(P)H).

There are no particular restrictions on the concentration of the various enzymes that are used in this kind of reaction system. The concentrations are decided so as to be appropriate for the reaction conditions and assay apparatus that are to be used. The concentration of the acidic aromatic compounds in the reaction mixture depends on the kind of biological samples that is to be assayed, but in general, this concentration is 10-500 mM, and preferably 50-200 mM. When the concentration is too low, error will arise in the measurement of the polyamines because of the reducing substances that are present in the biological sample. For example, when a system is used that develops color of formazan dye described below, the color will be excessively dark, and it will not be possible to obtain accurate measurements of the polyamines. When there is an excessively high concentration, the enzyme reactions will be inhibited. The pH of the reaction system is generally about 4-10, and the concentration chosen for the NAD(P)+ is a concentration that will give a maximum extent of reaction by the aminoalkylaldehyde dehydrogenase (for example, ABAL-DH), which is also a concentration that will not inhibit the other enzymes in the reaction system; the concentration is preferably 0.1-20 mM. Ordinarily, the reaction is carried out in a suitable buffer. The temperature of the reaction is selected with consideration for the optimum temperature of the enzymes used and the like. Generally, the reaction temperature can be set at 20°-40° C.

The NAD(P)H that is produced in the above reaction is measured by, for example, the direct colorimetric method by optical density at 340 nm, and the amount of polyamines in the biological sample can be calculated from the values obtained. Alternatively, a reaction of NAD(P)H with other substances is carried out, and the NAD(P)H is measured indirectly by the measurement of the products of that reaction, from which results the amount of polyamines can be calculated.

In one method in which NAD(P)H is measured, formazan dye produced by the reaction of formazan reagent (i.e., tetrazolium salts) and NAD(P)H in the presence of electron carrier is determined. As the electron carrier, for example, phenazine methosulfate, 1-methoxyphenazine methosulfate, diaphorase, etc., can be used. There are no particular limits on the concentration of the electron carrier to be used, but it is preferable that the concentration in the reaction system is 0.1 mM or more. When diaphorase is to be used, 0.1 U/ml or more is suitable.

As the formazan reagent, for example, nitrotetrazolium blue (NTB), 3-(p-iodophenyl)-2-(p-nitrophenyl)-5-phenyltetrazolium (INT), and 3-(4,5-dimethylthiazol-2-yl)-2,5-diphenyltetrazolium bromide (MTT), etc., can be used. There are not particular limitations on the concentration of these compounds to be used, but it is preferable that the concentration in the reaction system is 0.05-5 mM. In the assay system that uses a formazan reagent, electrons are provided to the formazan reagent from NAD(P)H via an electron carrier, by which means the formazan reagent is reduced, resulting in a formazan dye. The formazan dye has a higher molecular absorption coefficient than that of NAD(P)H. Therefore, it can be measured spectrophotometrically with great sensitivity.

In a different method, resazurin is reacted with NAD(P)H in the presence of an electron carrier, and the resorufin that is produced can be measured by its fluorescence. In yet another method, flavin reductase (FR) is reacted with NAD(P)H in the presence of flavin mononucleotide (FMN), and the reduced FMN that is produced is treated with luciferase from luminescent bacteria, then the luminescence produced can be measured. As the FR and LCF, enzymes from luminescent bacteria can be used.

In the measuring method of this invention, instead of there being separate steps of a reaction that gives rise to aminoalkylaldehydes from polyamines and the use of aminoalkylaldehyde dehydrogenase in the presence of $NAD(P)^+$ to give NAD(P)H as described above, it is also possible to add the enzymes and the reagents (including acidic aromatic compounds) to the sample solution at the same time, so that the reactions take place in a single step. Also, when NAD(P)H is measured by a coloration reaction, fluorescence reaction, or luminescence reaction, the enzymes and reagents used for this reaction can be added to the reaction system after the production of NAD(P)H, or can be added to the sample solution with DAO, etc., at the start of the reaction.

In the method for the measurement of polyamines of this invention, because an acidic aromatic compound is present in the reaction system, it is possible to measure the polyamines with high accuracy without the influence of reducing substances in the biological sample. For that reason, there is no need for the step of removal of reducing substances, for example, by use of an cationic-exchange column. In this way, the reaction can be carried out in a single step, so it is possible to use this method for the assay of polyamines in an automated analyzer. The method of this invention can be used for the assay of polyamines in urine samples that contain particularly large amounts of reducing substances.

EXAMPLES

Below, this invention will be explained by reference to examples.

EXAMPLE 1

Polyamines in urine were measured with an automated analyzer by use of the formazan coloration method.

The automated analyzer used in measurement was a Hitachi Model 705 automated analyzer (Hitachi Ltd.); changes in optical density at the time of assay were continuously monitored by computer. The reagents used in the assay were of the following compositions.

| Reagent composition | |
|---|---|
| | (Final concentration) |
| (a) Reagent 1 | |
| Good buffer, pH 7.0 | 0.2 M |
| Triton X-100 | 1.0% |
| Ascorbate oxidase | 3.3 U/ml |
| APAH | 5 U/ml |
| MTT | 20 μg/ml |
| Diaphorase | 3 U/ml |
| Putrescine oxidase | 15 U/ml |
| Benzenesulfonic acid | 0.1 M |
| (b) Reagent 2 | |
| Good buffer, pH 7.0 | 0.2 M |
| Triton X-100 | 1.0% |
| ABAL-DH | 0.5 U/ml |

-continued

| Reagent composition | |
|---|---|
| | (Final concentration) |
| $NAD^+$ | 1 mM |

These reagents were provided for the automated analyzer, and urine samples were put in the analyzer. The reagent volume and sample volume used for each measurement in the automated analyzer were as follows: reagent 1, 350 μl; reagent 2, 50 μl; and urine sample, 20 μl. The volume, 20 μl, of urine samples that was used was the volume that gives the greatest sensitivity (relative sensitivity) by this automated analyzer. The other assay conditions were a reaction temperature of 37° C., a reaction time of 10 minutes, and the measurement wavelength of 570 nm.

Results of the assays of two different urine samples, A and B, are shown in FIG. 1. In a separate experiment, reagent 1 that did not contain benzene sulfonic acid (i.e., the acidic aromatic compound) was prepared, and this reagent was used in the assay of urine sample B. The results are shown as curve C in FIG. 1. FIG. 1 shows that when reagent 1 contained benzene sulfonic acid as the acidic aromatic compound, the optical density of the sample blank did not increase. The reason is that the increase in optical density that might arise from the reducing substances is suppressed. That is, accurate measurements of the polyamines in urine were performed without any effect from reducing substances.

EXAMPLE 2

Figure 2:
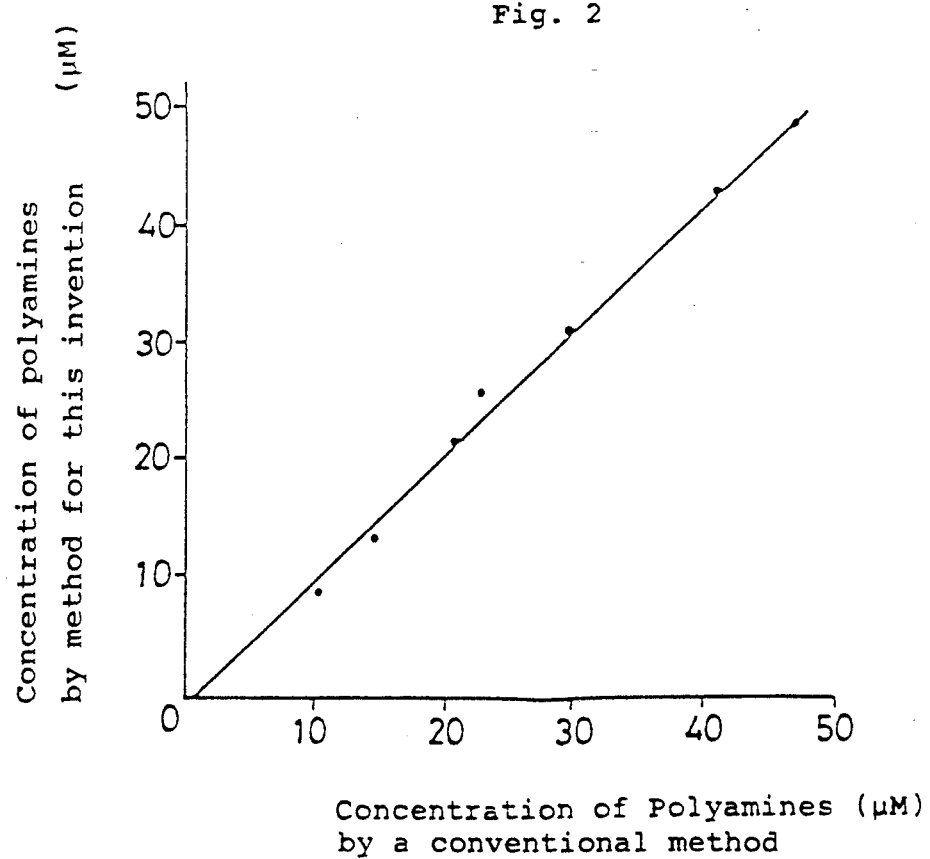
FIG. 2 is a graph that shows the correlation of values obtained by the method of this invention and by a conventional method that uses a column.

Seven different urine samples with different polyamine concentrations were assayed for the concentration of polyamines according to the method of Example 1 using the automated analyzer (Hitachi Model 705; Hitachi Ltd.). The assay mode of the automated analyzer was the N-N method, and automatic correction was made with a sample blank. In a separate experiment, as a conventional method, *Polyamine-Test-Enzyme*, a commercial polyamine assay kit, (Tokuyama Soda Co. Ltd.) was used, and 7 urine samples were assayed. Two portions of each of the above-mentioned samples, respectively, were subjected to a series of measurements by either the method of this invention or the conventional method. For each sample, the mean values were obtained from two measurements by either method. The results when sample solutions were measured according to this invention were plotted on the y-axis, and the results when the same sample solutions were measured with use of the commercially available kit were plotted on the x-axis. The graph obtained is shown in FIG. 2. The correlation of the values measured by the use of this invention with the values measured in the conventional way was r=0.997, and the correlation equation was y=1.059x−1.47, which indicates very good linear correlation.

EXAMPLE 3

For use as urine samples, the following sample solutions D, E, and F were prepared:
D Urine:water, 9:1 (by volume)
E Urine:aqueous solution of uric acid (50 mg/dl)=9:1 (by volume)
F Urine:aqueous solution of ascorbic acid (200 mg/dl)=9:1 (by volume)

These sample solutions D, E, and F were assayed according to the method of Example 1 except that the acidic aromatic compounds listed in Table 1 were used instead of the benzene sulfonic acid contained in reagent 1. The assay mode of the automated analyzer was the N-N method, and automatic correction was made with a sample blank.

The absorbance after 10 minutes of reaction is shown in Table 2.

TABLE 1

| Reagent | Acidic aromatic compound |
|---|---|
| I | Benzoic acid |
| II | Naphthalenesulfonic acid |
| III | Benzenesulfonic acid |
| IV | p-Chlorobenzoic acid |
| V | 2-Chloronaphthalenesulfonic acid |
| VI | 4-Hydroxynaphthalenesulfonic acid |
| VII | None |

TABLE 2

| | Optical Density | | | |
|---|---|---|---|---|
| Reagent | Blank | Sample Solution D* | Sample Solution E* | Sample Solution F* |
| I | 0.054 | 0.124 | 0.124 | 0.125 |
| II | 0.049 | 0.123 | 0.124 | 0.124 |
| III | 0.057 | 0.126 | 0.127 | 0.126 |
| IV | 0.056 | 0.123 | 0.125 | 0.123 |
| V | 0.047 | 0.127 | 0.126 | 0.126 |
| VI | 0.056 | 0.125 | 0.124 | 0.125 |
| VII | 0.050 | 0.125 | 0.142 | 0.138 |

*(measured value for sample solution) - (blank)

Table 2 shows that with the use of a reaction system in which a reagent that contains the above acidic aromatic compounds to assay sample solutions E and F, that contain reducing substances, there was no increase in absorbance caused by these reducing substances.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for measuring the amount of polyamines in a biological sample, comprising: adding to the biological sample aminoalkylaldehyde dehydrogenase, either NAD+ or NADP+, at least one of diamine oxidase and polyamine oxidase, and an acidic aromatic compound selected from the group consisting of benzene derivatives containing a carboxyl group or a sulfo group and naphthalene derivatives containing a carboxyl group of a sulfo group, wherein said acidic aromatic compound is present in a concentration of 10 to 500 mM; and measuring the polyamines in said biological sample in the presence of said acidic aromatic compound, by directly measuring the amount of NADH or NADPH produced or measuring the amount of products produced in a reaction of the NADH or NADPH.

2. A method as claimed in claim 1, wherein:
said adding comprises adding a first reagent to the biological sample, said first reagent containing said acidic aromatic compound and said at least one of diamine oxidase and polyamine oxidase, so that the polyamines are converted into aminoalkylaldehydes, and adding a second reagent to the reaction mixture, said second reagent containing the aminoalkyldehydrogenase and said NAD+ or NADP+, so that the NAD+ or NADP+ is reduced to NADH or NADPH, respectively; and
said measuring the polyamines in the biological sample comprises measuring either the amount of NADH or NADPH or the amount of products derived from the NADH or NADPH.

3. A method as claimed in claim 2, wherein the first and second reagents are added to the biological sample simultaneously.

4. A method as claimed in claim 1, wherein:
said adding comprises adding a first reagent to the biological sample, and first reagent containing said acidic aromatic compound, said aminoalkyladlehyde dehydrogenase and said NAD+ or NADP+, so that pre-existing aminoalkylaldehyde is oxidized with the formation of NADH or NADPH, respectively, as a blank reaction, and adding a second reagent, said second reagent containing said at least one of diamine oxidase and polyamine oxidase, so that the polyamines are converted into aminoalkylaldehyde and NAD' or NADP+ is reduced to NADH or NADPH, respectively; and
said measuring the polyamines in the biological sample comprises measuring either the amount of NADH or NADPH, or the amount of products derived from NADH or NADPH.

5. A reagent for measuring of the amount of polyamines in a biological sample, comprising aminoalkylaldehyde dehydrogenase, either NAD+ or NADP+, and at least one of diamine oxidase and polyamine oxidase, wherein said reagent further comprises an acidic aromatic compound selected from the group consisting of benzene derivatives containing a carboxyl group or a sulfo group and naphthalene derivatives containing a carboxyl group or a sulfo group.

6. A method as claimed in claim 4, wherein said first reagent further contains acylpolyamine amidohydrogenase so that acylpolyamines in the biological sample are converted to free polyamines.

* * * * *